US006722370B1

(12) United States Patent
Mann

(10) Patent No.: US 6,722,370 B1
(45) Date of Patent: Apr. 20, 2004

(54) DELIVERY OF A COMPOSITION TO THE LIVER BY UTILIZING THE PORTAL VEIN

(75) Inventor: Michael J. Mann, Newton, MA (US)

(73) Assignee: Corgentech, Inc., South San Francisco, CA (US)

( * ) Notice: Subject to any disclaimer, the term of this patent is extended or adjusted under 35 U.S.C. 154(b) by 0 days.

(21) Appl. No.: 09/118,645

(22) Filed: Jul. 17, 1998

(51) Int. Cl.[7] ............................................. A61B 19/00
(52) U.S. Cl. ...................................... 128/898; 604/508
(58) Field of Search .......................... 128/898; 604/508, 604/27, 28, 29

(56) References Cited

U.S. PATENT DOCUMENTS

| | | | | |
|---|---|---|---|---|
| 3,838,683 A | * | 10/1974 | Kolin | 128/2.05 |
| 5,069,662 A | * | 12/1991 | Bodden | 604/4 |
| 5,766,901 A | | 6/1998 | Mann et al. | |
| 6,024,703 A | * | 2/2000 | Zanelli et al. | 600/437 |
| 6,026,316 A | * | 2/2000 | Kucharczyk et al. | 600/420 |

OTHER PUBLICATIONS

Harnek j. et al, (1996) Isolated liver perfusion using percutaneous methods: an experimental study in the pig. Cardiovasc Intervent Radiol Nov.–Dec.; 19(6):418–22.*
Funaki et al., "Portal Vein Stenosis in Children with Segmental Liver Transplants: Treatment with Percutaneous Transhepatic Venoplasty," Am. J. Roentgenol, 165:161–165, 1995.
Haskal et al., "Transjugular Intrahepatic Transcaval Porto–systemic Shut: The Gun–Sight Approach," J. Vascular and Interventional Radiology 7:139–142, 1996.
Lencioni et al., "Portal Vein Thrombosis After Percutaneous Ethanol Injection for Hepatocellular Carcinoma: Value of Color Doppler Sonography in Distinguishing Chemical and Tumor Thrombi," Am. J. Roentgenol. 164:1125–1130, 1995.
Nagino et al., "Selective Percutaneous Transhepatic Embolization of the Portal Vein in Preparation for Extensive Liver Resection: The Ipsilateral Approach," Radiology 200:559–563, 1996.
Rabe et al., "Renal Tumor Infarction with Absolute Ethanol," Am. J. Roentgenol. 139:1139–1144, 1982.
Ravikumar et al., "Percutaneous Hepatic Vein Isolation and High–Dose Hepatic Arterial Infusion Chemotherapy for Unresectable Liver Tumors," J. Clin. Oncology 12:2723–2736, 1994.
Redvanly et al., "Malignant Hepatic Tumors: Safety of High–Dose Percutaneous Ethanol Ablation Therapy," Radiology 188:283–285, 1993.
Rossle et al., "The Transjugular Intrahepatic Portosystemic Stent–Shunt Procedure for Variceal Bleeding," New Eng. J. Med. 330:165–171, 1994.
Shimamura et al., "Efficacy and Safety of Preoperative Percutaneous Transhepatic Portal Embolization with Absolute Ethanol: A Clinical Study," Surgery 121:135–141, 1997.

* cited by examiner

Primary Examiner—Corrine McDermott
Assistant Examiner—Thomas Barrett
(74) Attorney, Agent, or Firm—Ginger R. Dreger, Esq.; Heller Ehrman White & McAuliffe, LLP

(57) ABSTRACT

In general, the invention features methods for delivering a composition to the liver in a non-surgical, percutaneous approach by utilizing the portal vein. Also disclosed are methods allowing for the liver-specific delivery of a composition.

34 Claims, 5 Drawing Sheets

DELIVERY OF A COMPOSITION TO THE LIVER BY UTILIZING THE PORTAL VEIN

BACKGROUND OF THE INVENTION

The invention relates to the delivery of a composition to the liver.

The liver is one of the largest visceral organ in the body; in the average adult man, the liver weighs about 1.5 kilograms. The basic functions of this multi-functional organ can be divided into three groups: vascular functions for the storage and filtration of blood; a secretory function for the secretion of bile into the gastrointestinal tract; and metabolic functions concerned with the majority of the metabolic systems of the body.

The liver receives its blood supply from two major sources, the portal vein and the hepatic artery. The schematic representation of the liver shown in FIG. 1 depicts the major vessels of the liver. Note that the hepatic artery and portal vein supply blood to the liver, while the hepatic vein, which drains into the vena cava, removes blood from the liver.

About 1100 mL of portal blood enters the liver each minute via the portal vein. The portal vein is generally formed by the convergence of the splenic and superior mesenteric veins. In addition to the portal blood flow, approximately 350 mL of blood flows into the liver each minute through the hepatic artery. The portal blood flow is controlled by the various factors that determine flow through the gastrointestinal tract and the spleen.

The hepatic vein drains into the inferior vena cava, which contacts and is partly surrounded by the posterior surface of the liver. At any point in time, the normal blood volume of the liver, including the blood in the hepatic vein and the hepatic sinuses, is about 500 mL. Because the liver is an expandable and compressible organ, the liver can additionally store or release large quantities of blood. For example, when high pressure in the right atrium causes back pressure in the liver, the liver expands, and as much as 1 L of extra blood may be stored in the hepatic veins and sinuses. Likewise, in times of diminished blood volume, the liver may compress, thereby releasing extra blood into the circulatory system.

There are many diseases associated with the liver which affect one or more of the organ's functions. These diseases include hepatitis, cancer, cirrhosis, biliary atresia, cholestasis, and fatty liver. A process for facilitating delivery of a composition (e.g., a drug) to the liver would be useful in treating, or at least alleviating the symptoms of, a disease of the liver.

SUMMARY OF THE INVENTION

In general, the invention features a method and apparatus for facilitating delivery of a composition to the liver via a non-surgical percutaneous approach that utilizes the portal vein.

In a first aspect, the invention features a method for delivering a composition to a liver via the portal vein that includes the steps of: (a) inserting a first catheter into the portal vein via a non-surgical percutaneous route, wherein the first catheter includes a deployable means (e.g., a balloon) for occluding the portal vein; (b) inserting a second catheter into a blood vessel draining the liver, wherein the second catheter includes a deployable means (e.g., a balloon) for occluding the blood vessel draining the liver; and (c) delivering the composition to the liver via a delivery catheter that is either the first catheter or the second catheter.

In one embodiment of the first aspect of the invention, the composition delivered to the liver by the delivery catheter is collected by a collecting catheter that is either the first catheter or the second catheter, wherein the delivery catheter and the collecting catheter are different. In another embodiment, the delivery catheter is connected to the collecting catheter, such that the composition collected by the collecting catheter is returned to the liver by the delivery catheter.

In other embodiments of the first aspect of the invention, at least one of the first catheter and the second catheter is adapted for insertion via a conventional introducer sheathe, is adapted for insertion over a guidewire, is equipped with a gauge for monitoring pressure, is equipped with a flow meter for monitoring flow rate, or is at least in part radio-opaque.

In a second aspect, the invention features a method for delivering a composition to a liver via the portal vein that includes the steps of: (a) inserting a first catheter into the portal vein via a non-surgical percutaneous route, wherein the first catheter includes a deployable means (e.g., a balloon) for occluding the portal vein; (b) inserting a second catheter into a blood vessel draining the liver, wherein the second catheter includes a deployable means (e.g., a balloon) for occluding the blood vessel draining the liver; (c) inserting, into a blood vessel, other than the portal vein, supplying the liver, a third catheter that includes a deployable means (e.g., a balloon) for occluding the blood vessel, other than the portal vein, supplying the liver; and (d) delivering the composition to the liver via a delivery catheter that is either the first catheter, the second catheter, the third catheter, the first and the second catheters, the first and the third catheters, or the second and the third catheters, wherein the composition delivered to the liver by the delivery catheter is collected by a collecting catheter that is either the first catheter, the second catheter, the third catheter, the first and the second catheter, the second and the third catheter, or the first and the third catheter, and wherein the delivery catheter and the collecting catheter are different.

In one embodiment of the second aspect of the invention, at least part of the delivery catheter is connected to at least part of the collecting catheter, such that the composition collected by the collecting catheter is returned to the liver by the delivery catheter. In another embodiment, the blood vessel, other than the portal vein, supplying the liver is the hepatic artery. In other embodiments of the second aspect of the invention, at least one of the first catheter, the second catheter, and the third catheter is adapted for insertion via a conventional introducer sheathe, is adapted for insertion over a guidewire, is equipped with a gauge for monitoring pressure; is equipped with a flow meter for monitoring flow rate, or is at least in part radio-opaque.

In another embodiment of the first and second aspect of the invention, the first catheter includes a means (e.g., a port that is in communication with a lumen) for collecting blood flowing into the portal vein. In another embodiment, the means for collecting blood flowing into the portal vein of the first catheter is connected to a fourth catheter, which may be inserted into a blood vessel that does not supply the liver and may include a means (e.g., a port that is in communication with a lumen) for delivering blood into the blood vessel that does not supply the liver. In yet another embodiment, the first catheter includes a port that is proximal to the deployable means for occluding the portal vein of the first catheter.

In other embodiments of the first and second aspect of the invention, the blood vessel draining the liver is the hepatic vein, and the second catheter may further include a port that is distal to the deployable means for occluding the hepatic vein of the second catheter. In other embodiments, the blood vessel draining the liver is the vena cava, and the second catheter may further include a second, different deployable means for occluding the vena cava and a port located between each of the deployable means for occluding the vena cava of the second catheter, and the second catheter may further include a means for allowing continuous blood flow through the vena cava, such as a means that includes a first port located distal to both of the deployable means for occluding the vena cava of the second catheter, a second port located proximal to both of the deployable means for occluding the vena cava of the second catheter, and a lumen that allows communication between the first port and the second port.

In various other embodiments of the first and second aspects of the invention, the non-surgical percutaneous route is visualized by ultrasound guidance, is visualized by radiographic guidance, is visualized by magnetic resonance guidance, is an intravenous intrahepatic approach, or is a transcutaneous transhepatic approach.

In a third aspect, the invention features a method for delivering a drug to a liver that utilizes the portal vein that includes the steps of: (a) inserting a catheter into the portal vein via a non-surgical percutaneous route, wherein the catheter includes a deployable means (e.g., a balloon) for occluding the portal vein; and (b) delivering the drug to the liver via the catheter.

In various embodiments of the third aspect of the invention, the non-surgical percutaneous route is visualized by ultrasound guidance, is visualized by radiographic guidance, is visualized by magnetic resonance guidance, is an intravenous intrahepatic approach, or is a transcutaneous transhepatic approach. In other embodiments, the catheter is adapted for insertion via a conventional introducer sheathe, is adapted for insertion over a guidewire, is equipped with a gauge for monitoring pressure, is equipped with a flow meter for monitoring flow rate, or is at least in part radio-opaque.

By "drug" is meant a compound or composition that acts as a therapeutic, diagnostic, or preventive agent on a liver cell. A drug may produce a metabolic or phenotypic change in a liver cell, may alter the growth of a liver cell, may influence a liver cell's interactions with other cells, may influence the genetic make-up or genetic activity of a liver cell, or may result in the death of a liver cell. For the purposes of the invention, a drug specifically excludes any compound or composition administered at a dosage or delivered at a concentration sufficient to either impede blood flow through the hepatic vasculature (e.g., ethanol or other embolization agents) or facilitate blood flow though the hepatic vasculature (e.g., heparin).

By "liver cell" is meant a cell that is located in the liver. Liver cells include, without limitation, cancerous liver cells, hepatocytes, Kupffer cells, Ito cells, endothelial cells lining the hepatic sinusoids, vascular endothelial cells lining the hepatic blood vessels, and any cells of any origin which happen to reside in the liver (e.g., metastatic cancer cells of ectopic origin).

By "proximal" is meant that a catheter feature is closer to the person administering the catheter than a reference object. For example, a feature (e.g., a port) located proximal to a reference object (e.g., an occluding device) is closer to the person administering the catheter than the reference object. Hence, the feature is located between the person administering the catheter and the reference object.

By "distal" is meant that a catheter feature is more distant from the person administering the catheter than a reference object. For example, a feature (e.g., a port) located distal to a reference object (e.g., an occluding device) is farther from the person administering the catheter than the reference object. Hence, the reference object is located between the person administering the catheter and the feature.

The invention described herein provides methods for delivering a composition to the liver via the portal vein by using a non-surgical, percutaneous approach. The invention also features method for the liver-specific delivery of a composition. By localizing the delivery of a composition to the liver, a higher concentration of a composition (e.g., a drug) may be administered than would have been administered systemically due to, for example, toxicity of the composition to other areas of the body (e.g., the bone marrow compartment).

Other features and advantages of the invention will be apparent from the following detailed description thereof, and from the claims.

DETAILED DESCRIPTION

Utilizing a non-surgical percutaneous approach that employs the major blood vessels of the liver, the present invention features delivery of a composition to the cells of the liver via the portal vein, either alone, or in combination with the hepatic vein, the hepatic artery, or both.

Apparatus for Delivering a Composition to the Liver

An apparatus for delivering a composition to liver cells has been developed which utilizes a series of catheters, one of which targets the portal vein of the liver. To deliver a composition to the cells of the liver, each of the catheters of the apparatus may be introduced into a major liver blood vessel either via a transcutaneous transhepatic approach or via an intravenous intrahepatic approach.

A) The Portal Vein Catheter

Figure 1:
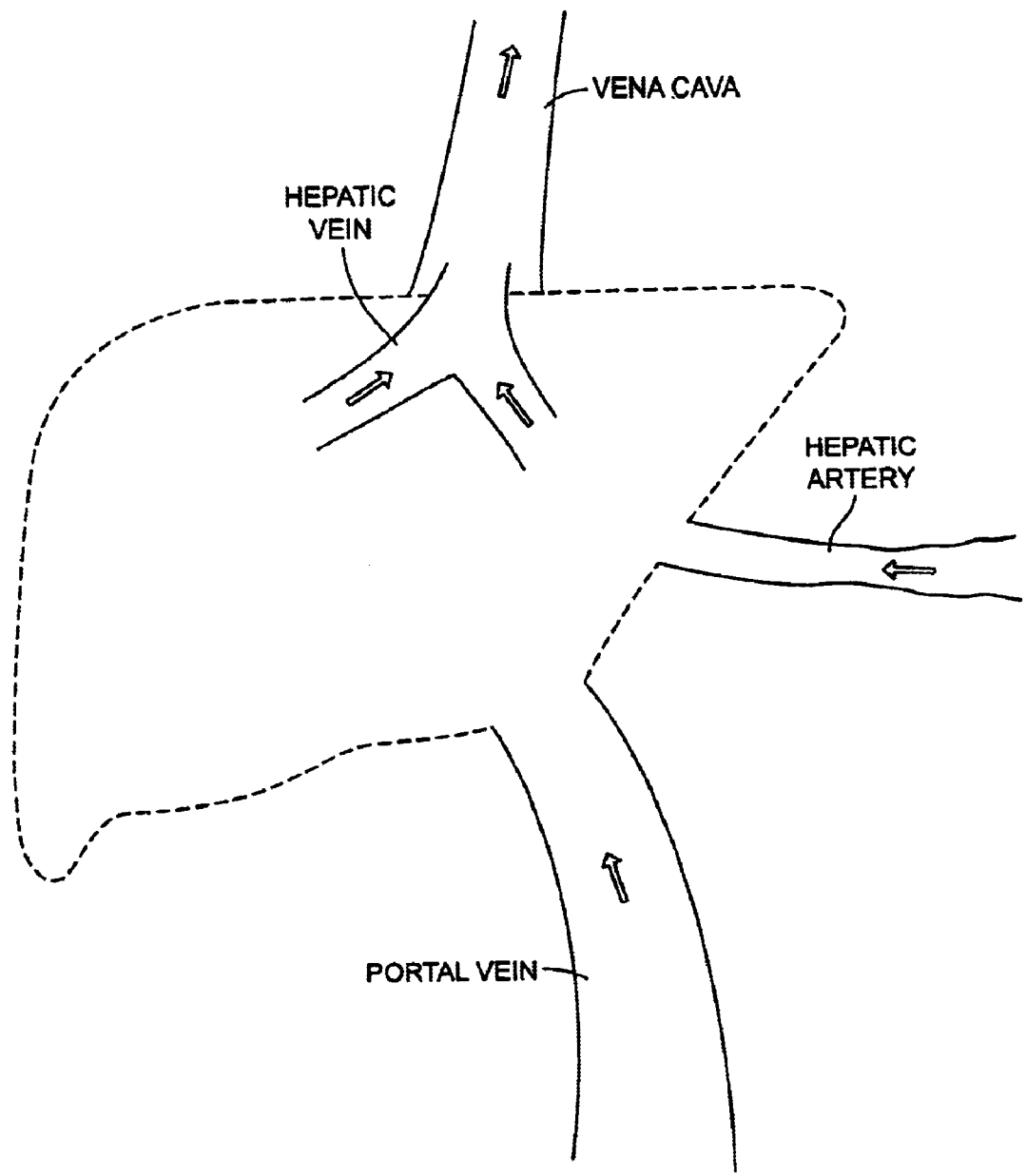
FIG. 1 is a schematic diagram of the major blood vessels of the liver. The liver itself is outlined with a dotted line. Direction of blood flow is depicted with arrows and, in general, flows from the bottom to the top in this figure. Blood flows into the liver via the hepatic artery and the portal vein, and exits the liver via the hepatic vein which flows into the vena cava.
Figure 2:
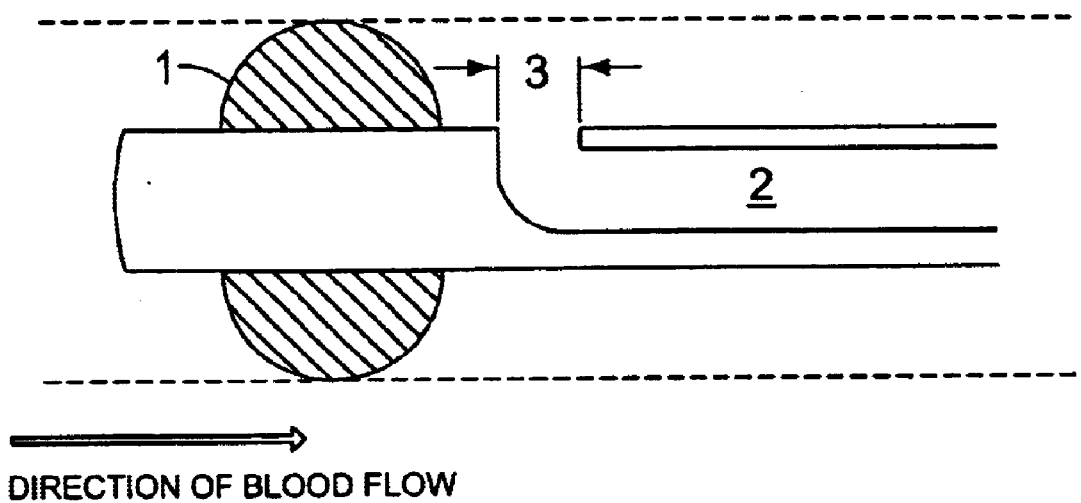
FIG. 2 is a schematic representation of a horizontal cross section of a portal vein catheter useful in the invention. Note that the deployable device (1), denoted as a cross-hatched section, is in the deployed position, and is firmly lodged against the wall of the portal vein, which is denoted as a dotted line. Additionally note that the direction of the flow of blood in the portal vein is from left to right in this figure.

A schematic diagram of a catheter that may be inserted into the portal vein is provided in FIG. 2. The portal vein catheter has a deployable occluding device (1) such as a balloon, that is mounted on the catheter. When deployed (the configuration depicted in FIG. 2), the deployable occluding device (1) occludes the portal vein, thereby halting blood flow in the portal vein. The deployed occluding device may additionally serve to prevent any undesired backflow of the composition being added to the liver into a region of the portal vein located distal the occluding device (i.e., to the left of the occluding device (1) shown in FIG. 2).

The portal vein catheter is further equipped with a lumen (2) for delivery of a fluid via a port (3) proximal to the occluding device (1) through which a composition can be delivered either in solution or suspension.

Figure 3:
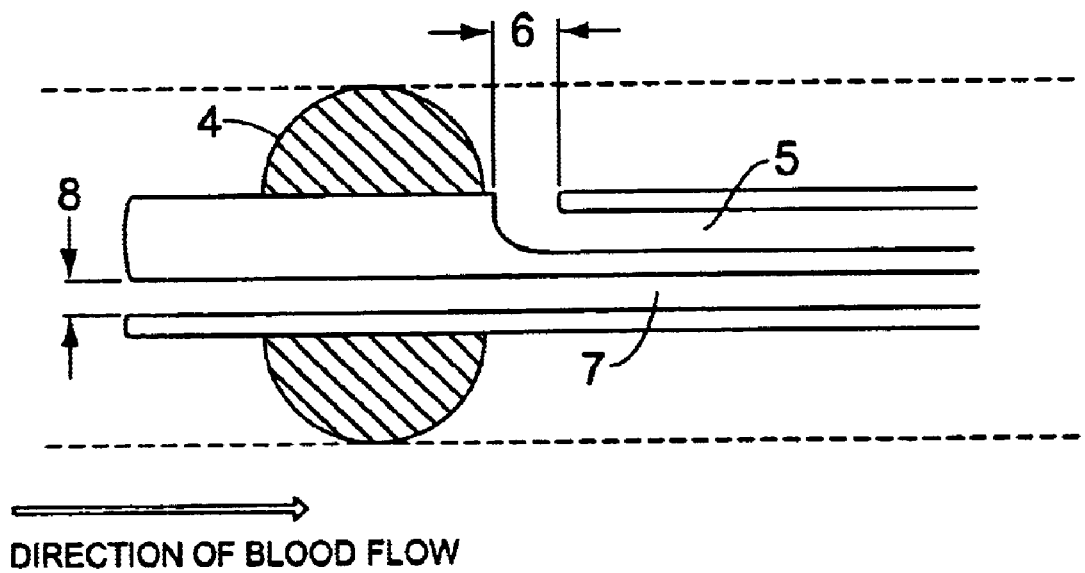
FIG. 3 is a schematic representation of a horizontal cross section of a second portal vein catheter useful in the invention. Note that the deployable occluding device (4), denoted as a cross-hatched section, is in the deployed position, and is firmly lodged against the wall of the portal vein, which is denoted as a dotted line. Additionally note that the direction of the flow of blood in the portal vein is from left to right in this figure.

A second type of portal vein catheter that is useful in the invention is schematically represented in FIG. 3 and is equipped with an occluding device (4); a first lumen (5) for delivery of a fluid via a port (6) proximal to the occluding device (4) through which a composition can be delivered either in solution or suspension; and a second lumen (7) that is in communication with a port (8) located at the distal end of the catheter beyond the occluding device (4) to allow collection of portal venous blood for reinfusion back into the central venous circulation if collateral flow is considered inadequate.

B) The Second Catheter

For liver-specific delivery, a second catheter is employed that allows the isolation of return flow from a blood vessel draining the liver, such as the common hepatic vein. The second catheter may be inserted into the vena cava (FIGS. 4 and 5), or may be inserted into the hepatic vein (FIG. 6). The second catheter, preferably, is connected to the portal vein catheter such that fluid exiting the liver and collected by the second catheter can be re-introduced into the liver via the portal vein catheter.

Figure 4:
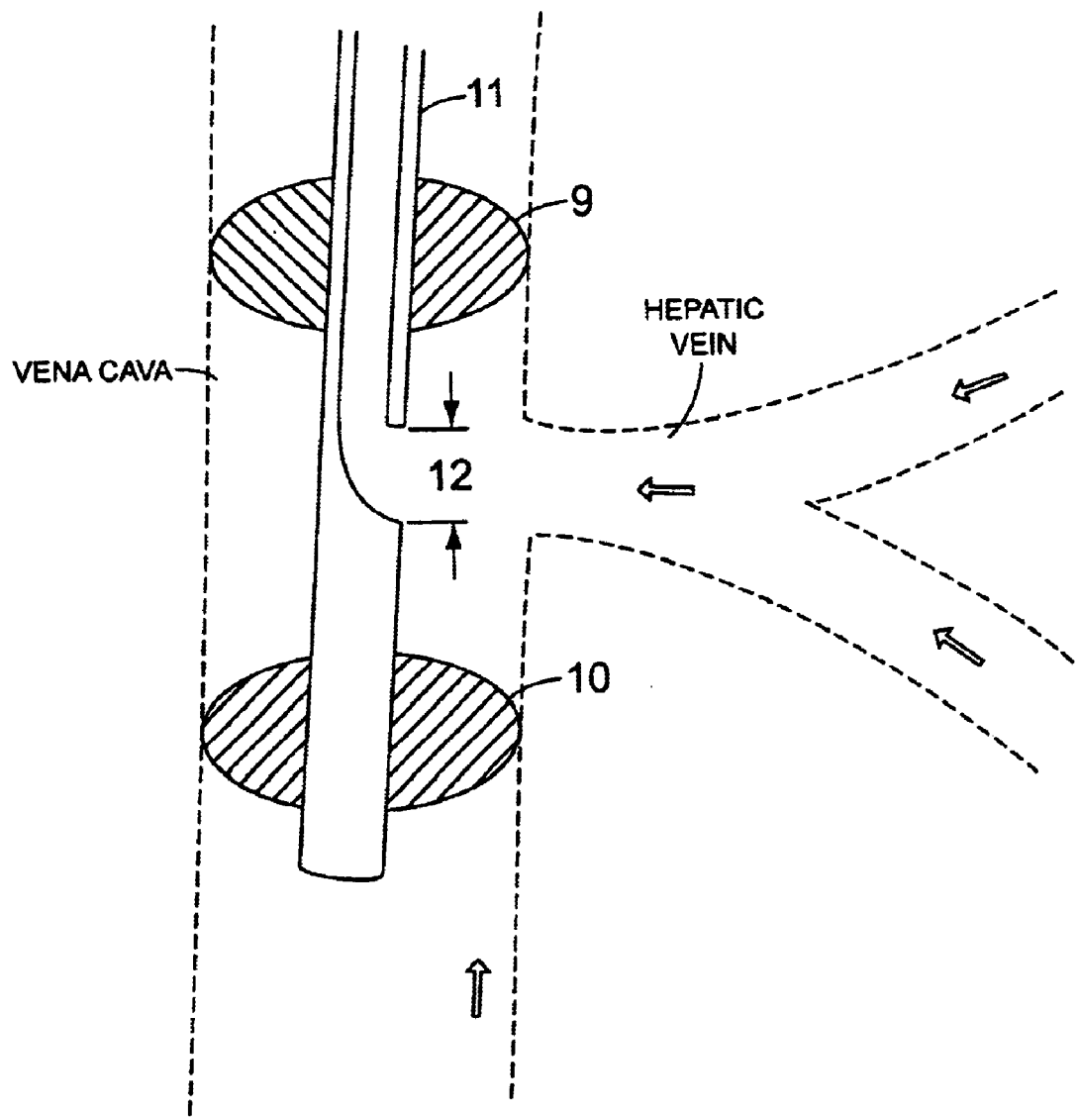
FIG. 4 is a schematic representation of a horizontal cross-section of a vena cava catheter. The dual occluding devices (9 and 10), denoted as the cross-hatched sections, are depicted in the deployed position and firmly lodge the catheter against the wall of the vena cava, which is denoted as a dotted line. Note that the direction of the flow of blood (depicted with arrows) is from right to left in the hepatic vein (as it drains into the vena cava) and from bottom to top in the vena cava.

The second catheter depicted in FIG. 4 is positioned in the vena cava at the point where the hepatic vein joins the vena cava. As shown in FIG. 4, the vena cava catheter is equipped with dual deployable occluding devices (9 and 10), and a lumen (11) that is in communication with a port (12) located between the dual deployable occluding devices (9 and 10) for the retrieval of a fluid (i.e., a composition) exiting the liver via the hepatic vein.

Figure 5:
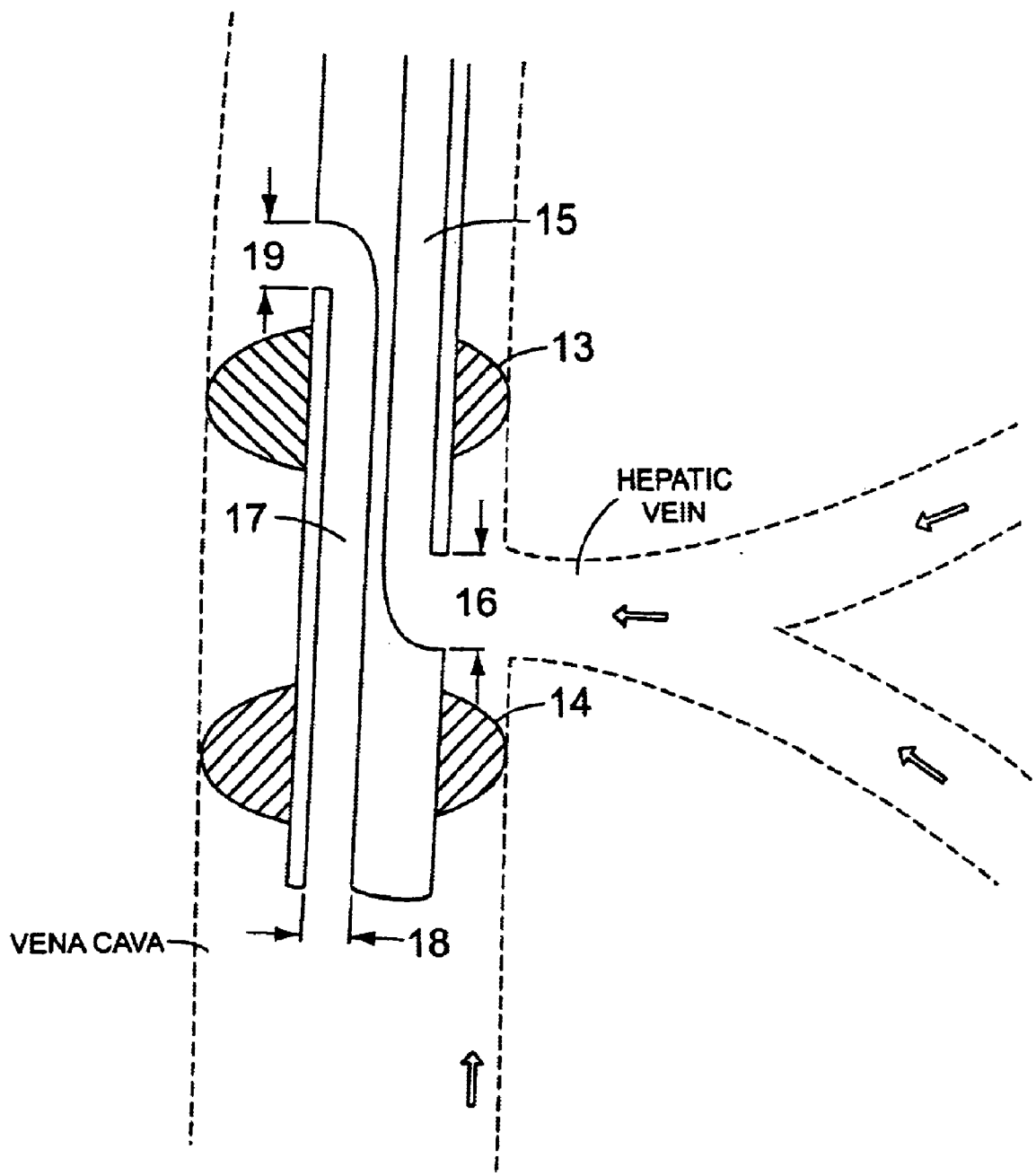
FIG. 5 is a schematic representation of a horizontal cross-section of a second type of vena cava catheter. The dual occluding devices (13 and 14), denoted as the cross-hatched sections, are depicted in the deployed position and firmly lodge the catheter against the wall of the vena cava, which is denoted as a dotted line. Note that the direction of the flow of blood (depicted with arrows) is from right to left in the hepatic vein (as it drains into the vena cava) and from bottom to top in the vena cava. The second lumen (17) is in communication with two ports (18 and 19) to allow continuous flow through the vena cava of blood draining non-liver tissues.
Figure 6:
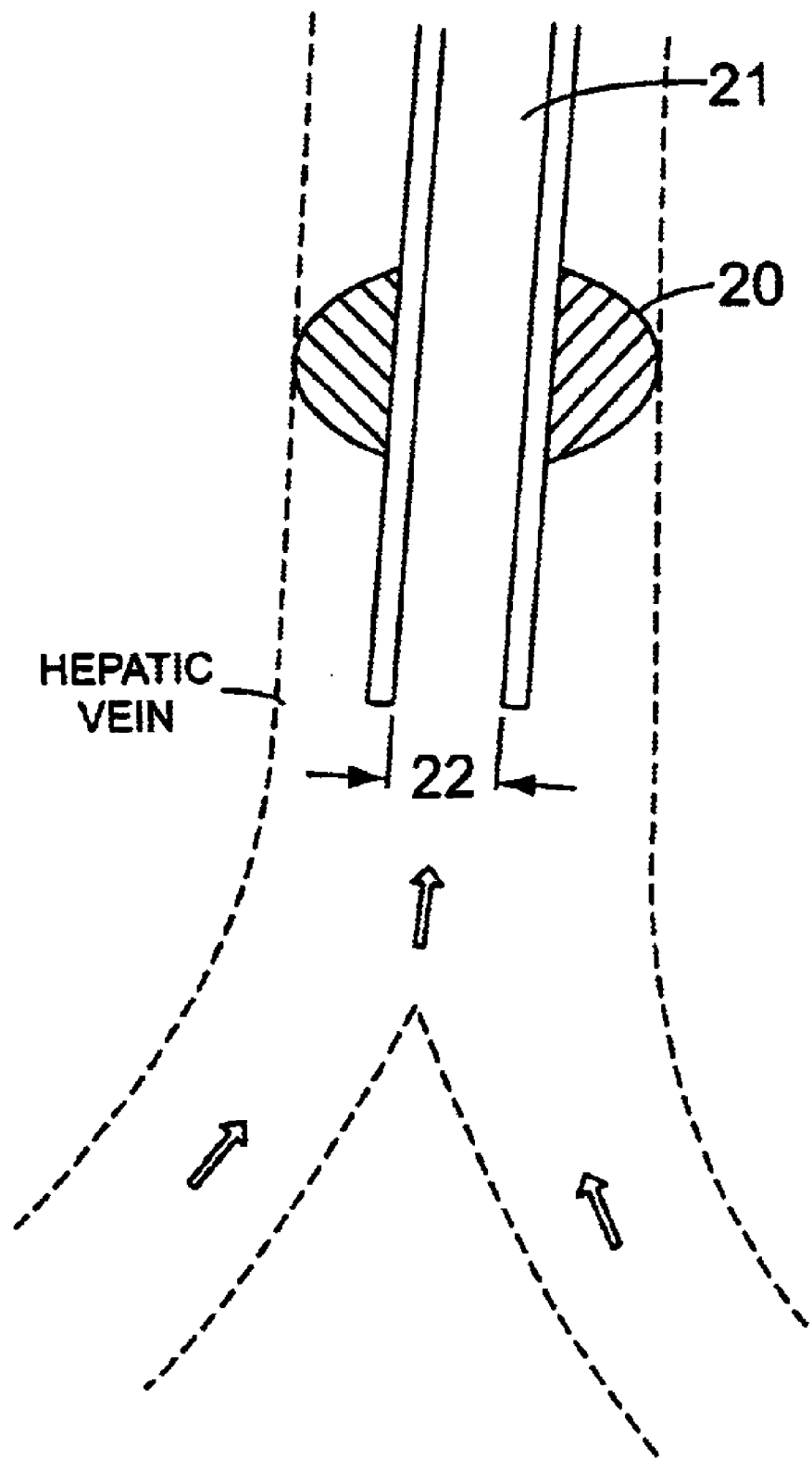
FIG. 6 is a schematic representation of a horizontal cross-section of a hepatic vein catheter. The occluding device (20), denoted as a cross-hatched section, is depicted in the deployed position and firmly lodges the catheter against the wall of the hepatic vein, which is denoted as a dotted line. Note that the direction of the flow of blood (depicted with arrows) is from bottom to top in this figure.

A second embodiment of the vena cava catheter is schematically represented in FIG. 5, and is equipped with dual deployable occluding devices (13 and 14); a first lumen (15) that is in communication with a port (16) located between the dual deployable occluding devices (13 and 14) through which a composition can be retrieved from the liver; a second lumen (17) that is in communication with a first port (18) located at the distal end of the catheter beyond both of the dual deployable occluding devices (13 and 14) and a second port (19) located proximal to both of the dual deployable occluding devices (13 and 14) to allow continuous flow in the vena cava for blood draining from tissues other than the liver.

The second catheter depicted in FIG. 6 is positioned in the hepatic vein, and has a single occluding device (20), and a lumen (21) that is in communication with a port (22) distal to the single occluding device (20) for the retrieval of a fluid (i.e., composition) exiting the liver via the hepatic vein.

C) The Optional Third Catheter

The apparatus and method of the invention may optionally include a third catheter equipped with a deployable occluding device that is placed in a blood vessel, other than the portal vein, which supplies blood to the liver. For example, a third catheter may be placed in the hepatic artery. The third catheter may be used merely to block blood flow into the liver via the hepatic artery by deploying the occluding device. This blockage may be desired to prevent the dilution of the composition being delivered to the liver by the first and/or second catheter by blood flowing into the liver via the hepatic artery.

Alternatively, the third catheter may have a lumen that is in communication with a fluid delivery port located distal to the occluding device. Once the artery is occluded when the occluding device is deployed, delivery of a composition can proceed through the hepatic artery via the lumen and fluid delivery port of the third catheter. Hence, the hepatic artery and/or the portal vein may be employed to deliver a composition to the liver, with collection of outflow via a hepatic vein catheter or a vena cava catheter. As with the portal vein catheter, the second catheter (i.e., the hepatic vein catheter or the vena cava catheter) may be connected to the hepatic artery catheter in such a way as to allow the outflow from the liver collected by the second catheters to be re-introduced to the liver via the hepatic artery catheter. Alternatively, should all three catheters be employed, the second catheter may be connected to both the portal vein catheter and the hepatic artery catheter such that outflow from the liver collected by the second catheter is re-introduced by both the hepatic artery catheter and the porta; vein catheter.

D) Catheter Modifications

The catheters forming the apparatus of the invention may be modified such that each catheter can preferably be introduced over guide wires and via conventional introducer sheathes. In addition, preferably each catheter is also partially radio-opaque to facilitate fluoroscopic guidance of catheter placement. The catheters described above are designed to carry fluids at sufficient flow rates to facilitate efficient composition delivery, including, without limitation, flow rates of between 100–5000 mL/min., preferably flow rates of between 250–3000 mL/min., and most preferably; flow rates of between 500–2000 mL/min. The catheters may be connected in circuits and combined with a pumping apparatus to allow uninterrupted flow of the composition as it enters, travels through, exits, and is re-introduced back into the liver. The catheters may be further equipped with gauges for monitoring pressure, thereby allowing an appropriate regulation of the pressure within the liver. Likewise, the catheters may be further equipped with flow meters for monitoring flow rates, thereby allowing an appropriate regulation of the flow rate of a composition being delivered to the liver.

A Method for Delivering a Composition to the Liver

Employing a portal vein catheter, a composition is delivered to the cells of the liver via the portal vein. By employing the multi-catheter apparatus described above, a composition is delivered to the liver in isolation, thereby preventing delivery of the composition to any non-liver cells. By this method, for example, a drug found to treat cirrhosis may be delivered in very high concentrations to the affected area without consideration for the effects of the drug on surrounding, unaffected non-liver tissue (e.g., the spleen). The method allows for control of the pressure and flow rate of the administered composition, as may be desired for both delivery to and enhanced uptake by cells within the liver.

In addition, given the liver's capacity to store fluid, it may be desired to administer a large quantity of a composition into an isolated liver, thus allowing the composition to distend the liver (but not to the point of damage), and then simply to allow the composition to remain in the liver for a desired period of time. With this approach, it may be desired to use the portal vein catheter depicted in FIG. 3, and allowing the collected blood flow from the portal vein to be routed into a vein not directly draining the liver, for example, the vena cava or the jugular vein (via a catheter with a delivery port that is in communication with the lumen (7) and port (8) of FIG. 3), thereby by-passing the liver, and yet not impeding blood flow to other areas of the body. Likewise, it may be desirable to use the vena cava catheter depicted in FIG. 5 in this approach, thereby allowing normal flow through the vena cava while by-passing the liver.

A Non-Surgical Percutaneous Approach

The invention allows complete percutaneous, minimally invasive, non-surgical isolation of the liver to facilitate delivery of a composition, and, additionally allows for control of pressure for intrahepatic composition delivery by simply regulating the flow rate at which a composition is added to the liver. Effluent from the second catheter (i.e., the hepatic vein catheter or the vena cava catheter) can be returned to the portal vein and/or hepatic artery catheter to allow recirculation for longer exposure of the liver to the administered composition, as well as the conservation of the composition (e.g., a therapeutic drug) and the delivery medium (e.g., blood or a physiologic solution).

A percutaneous approach is less invasive than surgical portal vein access, and therefore allows for a greater tolerance for the procedure in ill patients, a much faster recovery period with less associated morbidity and mortality, and fewer complications. True percutaneous isolation is significantly more effective at reducing the amount of composition "leaked" into the systemic circulation than either non-specific delivery or filtration, since the latter not only cannot be applied to all compositions, but is also limited with regard to filtration efficiency. With the improved isolation of composition delivery to the liver from systemic exposure that is provided by the invention, higher composition doses can be safely delivered to the liver, and pressurized delivery (see, e.g., Mann et al., PCT Publication No. W098/20109) can be exploited to enhance composition delivery and uptake for an improved therapeutic effect with fewer deleterious side effects and reduced morbidity.

Percutaneous approaches are well known to the ordinarily skilled physician, and are generally described in Ravikumar et al., J. Clin. Oncology 12: 2723–2736, 1994; Shimamura et al., Surgery 121: 135–141, 1997; Nagino et al., Radiology 200: 559–563, 1996; Lencioni et al., Amer. J. Roentgenol. 164: 1125–1130, 1995; Redvanly et al., Radiology 283–285, 1993; and Funaki et al., Amer. J. Roentgenol. 165: 161–165, 1995. To achieve a non-surgical, percutaneous approach for delivery of a catheter to a blood vessel of the liver (e.g., the portal vein), a transcutaneous transhepatic approach, or an intravenous intrahepatic approach may be employed. These approaches are discussed below.

A) Transcutaneous Transhepatic Approach

The transcutaneous transhepatic approach involves the direct puncture of the skin and the abdominal wall overlying the liver, and the subsequent puncture of the liver itself until a branch of the intrahepatic portal venous system is accessed. This puncture and catheter placement is preferably achieved with the guidance of an imaging modality, including, without limitation, ultrasound (e.g., two-dimensional or Doppler flow imaging), radiographic imaging (e.g., fluoroscopy or computed tomography), or magnetic resonance imaging. Conventional percutaneous access techniques such as guidewire manipulations and introducer sheathe insertions may then be utilized for the placement of the catheter into the portal venous system for movement into the appropriate position for delivery of a composition.

B) Intravenous Intrahepatic Approach

The intravenous intrahepatic approach involves accessing a peripheral venous structure, such as the jugular or femoral vein, with advancement of a catheter into the intrahepatic venous system, preferably using guidewire techniques and under the guidance of ultrasound imaging (e.g., two-dimensional or Doppler flow imaging), radiographic imaging (e.g., fluoroscopy or computed tomography), or magnetic resonance imaging. A puncture through the intrahepatic venous structure, through liver parenchyma and into an intrahepatic portal venous structure, is then accomplished. Catheter exchanges using conventional techniques may then be performed for the placement of the catheter into the portal vein using this intrahepatic access technique.

Retrograde Flow

In another variation, the invention described herein allows for a manipulation of the direction of flow utilized in the delivery of a composition to the liver. In vivo, blood flow through the liver proceeds from entry into the liver through the portal vein and hepatic artery, to exit the liver through the hepatic vein (which empties into the vena cava). By utilizing the methods of the invention, administration of a composition to the liver in a retrograde fashion is allowed. This technique may serve to deliver the administered composition to hard-to-reach areas of the liver. For example, a composition may be administered via the second catheter (e.g., the hepatic vein catheter or the vena cava catheter), allowed to flow through the liver in a direction opposite to that taken by normal blood, and collected as it exits the liver either via the hepatic artery, the portal vein, or both. The exiting composition may then be re-introduced into the liver via the second catheter.

In yet another variation of the invention, all of the catheters of the apparatus described above may be employed as points of entry for an administrated composition. This technique may serve to quickly flood the liver with the composition. Following administration, the composition then be allowed to remain in the liver for a desired period of time, as described above, or may be immediately drained from the liver. Drainage of a composition delivered to the liver by this approach is achieved by simply reversing the direction of flow of any of the catheters of the apparatus. If desired, the composition draining the liver may be collected, and possibly re-introduced into the liver via any of the catheters of the apparatus, as described above.

Compositions

The composition delivered to the liver using the method and apparatus of the invention may be any solution or suspension of a compound in a fluid. Methods well known in the art for making formulations are found, for example, in *Remington's Pharmaceutical Sciences* (18$^{th}$ edition), ed. A. Gennaro, 1990, Mack Publishing Company, Easton, Pa. Exemplary fluids include, without limitation, sterile water, physiological saline, or blood. If the liver is isolated for prolonged periods of time, an oxygen-carrying solution, such as blood, is preferably employed. In approaches in which the liver is isolated, and a composition is administered to the liver, allowed to passed through the liver, and then allowed to exit the liver, the composition is preferably in an oxygen-carrying solution which may be oxygenated while in transit ex vivo between the various catheters of the apparatus. Compositions of the invention include, without limitation, embolizing reagents, such as ethanol and fibrin-glue formulations; contrast agents, such as barium; drugs, such as chemotherapeutics and antibiotics; and suspensions of cells.

EXAMPLE I

A Method for Treating Amebiasis

Ambiasis of the liver, the most common extra-intestinal complication of infection with *Entamoeba histolytica*, leads to amebic abscesses. This disease may be treated with an antibiotic, such as metronidazole, using the methods of the invention. For example, employing fluoroscopic guidance and a standard guidewire technique (using a guidewire commercially available from, e.g., Microvena, White Bear Lake, Minn.), a 5–6 French catheter (commercially available from, e.g., Meditech, Watertown, Mass.) having a lumen and a deployable balloon is placed using a transcutaneous tran-shepatic approach into the portal vein. A second catheter also having a lumen and a deployable balloon, and of a size suited for the hepatic vein (e.g., 5-French) is placed into the hepatic vein. In addition, a third suitably-sized balloon catheter (e.g., 5-French) also having a lumen is placed into the hepatic artery.

The balloons on all three catheters are deployed, firmly lodging the catheters in the portal vein, hepatic vein, and hepatic artery. Sterile saline is administered through the portal vein and hepatic artery catheters, and the blood in the liver, displaced by the administered saline, is collected by the hepatic vein catheter and returned to the patient via a fourth catheter placed in a femoral vein. Following removal of the blood from the liver, the hepatic vein catheter is disconnected from the fourth catheter (which is removed from the femoral vein), and is connected to the portal vein and hepatic artery catheters such that the composition (e.g., saline) collected by the hepatic vein catheter is returned to the liver via the portal vein and hepatic artery catheters.

An amount of metronidazole hydrochloride (Flagyl I.V.; commercially available form Schiapparelli Searle) useful for treating ambiasis of the liver (e.g., 5–15 mg/kg initial dose, with a 2.5–7.5 mg/kg follow-up dosage) is then administered through the portal vein and hepatic artery catheters, collected by the hepatic vein catheter, and is returned to the liver via the portal vein and hepatic artery catheters. The metronidazole hydrochloride is perfused through the liver for an hour. The hepatic vein catheter is then disconnected from the portal vein and hepatic artery catheters, the portal vein and hepatic artery catheters are flushed with saline, and the effluent metronidazole hydrochloride and saline is collected by the hepatic vein catheter and discarded. The balloons of all three catheters are then deflated, and the catheters are removed. If required, this metronidazole hydrochloride administration is repeated until the amebic abscesses of the liver are reduced.

It will be understood, of course, that the size of the catheters and the dosage of antibiotic used will vary in accordance with the patient (e.g., smaller catheters are used on a child).

EXAMPLE II

A Method for Treating Multiple Hepatic Metastasis of Colorectal Carcinoma

Patients with multiple hepatic metastasis of colorectal carcinoma may also be treated with the methods provided herein. In this example, a 5–6 French balloon catheter, such as the catheter depicted on FIG. 3, is inserted into the portal vein of a patient using an intravenous intrahepatic approach. A second balloon 6–20 French catheter, such as the catheter depicted in FIG. 5, is inserted into the femoral vein, and is advanced into the vena cava to the point where the hepatic vein joins the vena cava. A third balloon catheter lacking a lumen is placed into the hepatic artery. The portal vein catheter is connected to a fourth balloon catheter that is inserted into the jugular vein such that blood flowing into the portal vein is collected by the portal vein catheter and delivered to the jugular vein via the fourth catheter.

The balloons on all four catheters are deployed, firmly lodging the catheters in the portal vein, vena cava, hepatic artery, and the jugular vein. The second catheter is next connected to the portal vein catheter such that a composition administered to the liver by the second catheter is collected by the portal vein catheter and returned to the liver via the second catheter. An amount of 5-fluorouracil (i.e., 5-FU) that is useful for treating multiple hepatic metastasis of colorectal carcinoma (e.g., 1,000–5,000 mg/m$^2$) is mixed with an amount of blood sufficient to completely saturate the liver (e.g., 2 L). Most preferably, the blood is from the patient, less preferably, the blood is from a cross-matched donor.

The blood/5-FU composition is then added to the liver via the second catheter, and allowed to recirculate through the second catheter and the portal vein catheter for several hours. As the blood/5-FU circulates ex vivo between the second and portal vein catheters, the blood cells are preferably oxygenated, as during standard cardiopulmonary by-pass surgery. Following treatment, the second catheter is disconnected from the portal vein catheter. The second catheter is then flooded with sterile saline, and the effluent blood/5-FU is collected by the portal vein catheter and may be either saved or discarded. The balloons of all four catheters are deflated, and the catheters are removed. The 5-FU treatment is repeated as necessary.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the claims.

What is claimed is:

1. A method for delivering a therapeutic composition to the liver of a subject, said method comprising the steps of:
   (a) inserting a first catheter into the portal vein of said subject via a non-surgical percutaneous route wherein said first catheter comprises a deployable mechanism for occluding said portal vein;
   (b) inserting a second catheter into a blood vessel draining said liver, wherein said second catheter comprises a deployable mechanism for occluding said blood vessel draining said liver;
   (c) delivering said therapeutic composition to said liver via a delivery catheter selected from the group consisting of said first catheter and said second catheter; and
   (d) collecting said therapeutic composition by a collecting catheter selected from the group consisting of said first catheter and said second catheter, wherein said delivery catheter and said collecting catheter are different.

2. The method of claim 1, wherein said composition delivered to said liver by said delivery catheter is collected by a collecting catheter selected from the group consisting of said first catheter and said second catheter, wherein said delivery catheter and said collecting catheter are different.

3. The method of claim 2, wherein said delivery catheter is connected said collecting catheter whereby said therapeutic composition collected by said collecting catheter is returned to said liver by said delivery catheter.

4. The method of claim 1, wherein at least one of said first catheter and said second catheter is adapted for insertion via a conventional introducer sheath.

5. The method of claim 1, wherein at least one of said first catheter and said second catheter is adapted for insertion over a guidewire.

6. The method of claim 1, wherein at least one of said first catheter and said second catheter is equipped with a gauge for monitoring pressure.

7. The method of claim 1, wherein at least one of said first catheter and said second catheter is equipped with a flow meter for monitoring flow rate.

8. The method of claim 1, wherein at least one of said first catheter and said second catheter is at least in part radio-opaque.

9. A method for delivering a therapeutic composition to the liver of a subject, said method comprising the steps of:
   (a) inserting a first catheter into the portal vein of said subject via a non-surgical percutaneous route, wherein said first catheter comprises a deployable mechanism for occluding said portal vein;
   (b) inserting a second catheter into a blood vessel draining said liver, wherein said second catheter comprises a deployable mechanism for occluding said blood vessel draining said liver;
   (c) inserting, into a blood vessel, other than the portal vein, supplying said liver, a third catheter that comprises a deployable mechanism for occluding said blood vessel, other than the portal vein, supplying said liver;
   (d) delivering said therapeutic composition to said liver via a delivery catheter or catheters selected from the group consisting of said first catheter, said second catheter, said third catheter, said first and said second catheters, said first and said third catheters, and said second and said third catheters; and
   (e) collecting said therapeutic composition by a collecting catheter or catheters selected from the group consisting of said first catheter, said second catheter, said third catheter, said first and said second catheter, said second and said third catheters, and said first and said third catheters, wherein said delivery catheter or catheters and said collecting catheter or catheters are different, and when said therapeutic composition is delivered through said second catheter, it is collected by said first catheter or said first catheter and said third catheter, and when said therapeutic composition is delivered through said third catheter, it is collected by said first catheter or said first catheter and said second catheter.

10. The method of claim 9, wherein at least part of said delivery catheter is connected to at least part of said collecting catheter, whereby said therapeutic composition collected by said collecting catheter is returned to said liver by said delivery catheter.

11. The method of claim 9, wherein at least one of said first catheter, said second catheter, and said third catheter is adapted for insertion via a conventional introducer sheath.

12. The method of claim 9, wherein at least one of said first catheter, said second catheter, and said third catheter is adapted for insertion over a guidewire.

13. The method of claim 9, wherein at least one of said first catheter, said second catheter, and said third catheter is equipped with a gauge for monitoring pressure.

14. The method of claim 9, wherein at least one of said first catheter, said second catheter, and said third catheter is equipped with a flow meter for monitoring flow rate.

15. The method of claim 9, wherein at least one of said first catheter, said second catheter, and said third catheter is at least in part radio-opaque.

16. The method of claim 9, wherein said blood vessel, other than the portal vein, supplying said liver is the hepatic artery.

17. The method of claim 9, wherein delivery of said therapeutic composition to said liver is enhanced by use of pressure.

18. The method of claim 1 or 9, wherein said first catheter further comprises a means for collecting blood flowing into said portal vein.

19. The method of claim 18, wherein said means for collecting blood flowing into said portal vein of said first catheter is connected to a fourth catheter.

20. The method of claim 19, wherein said fourth catheter is inserted into a blood vessel that does not supply said liver and comprises a means for delivering blood into said blood vessel that does not supply said liver.

21. The method of claim 1 or 9, wherein said first catheter further comprises a port that is proximal to said deployable means for occluding said portal vein of said first catheter.

22. The method of claim 1 or 9, wherein said blood vessel draining said liver is the hepatic vein.

23. The method of claim 22, wherein said second catheter further comprises a port that is distal to said deployable mechanism for occluding said hepatic vein.

24. The method of claim 1 or 9, wherein said blood vessel draining said liver is the vena cava.

25. The method of claim 24, wherein said second catheter further comprises a second, different deployable mechanism for occluding said vena cava and a port located between each of said deployable mechanisms for occluding said vena cava.

26. The method of claim 25, wherein said second catheter further comprises a means for allowing continuous blood flow through said vena cava.

27. The method of claim 26, wherein said means for allowing continuous blood flow through said vena cava comprises a first port located distal to both of said deployable mechanisms for occluding said vena cava of said second catheter, a second port located proximal to both of said deployable mechanisms for occluding said vena cava of said second catheter, and a lumen that allows communication between said first port and said second port.

28. The method of claim 1 or 9, wherein said non-surgical percutaneous route is visualized by ultrasound guidance.

29. The method of claim 1 or 9, wherein said non-surgical percutaneous route is visualized by radiographic guidance.

30. The method of claim 1 or 9, wherein said non-surgical percutaneous route is visualized by magnetic resonance guidance.

31. The method of claim 1 or 9, wherein said non-surgical percutaneous route is an intravenous intrahepatic approach.

32. The method of claim 1 or 9, wherein said non-surgical percutaneous route is a transcutaneous transhepatic approach.

33. The method of claim 1 or 9, wherein said therapeutic composition is delivered to said liver via said vessel draining said liver.

34. The method of claim 1 or 9, wherein said therapeutic composition is discarded after delivery to and drainage from said liver.

* * * * *